US008730314B2

(12) United States Patent
Hannibal et al.

(10) Patent No.: US 8,730,314 B2
(45) Date of Patent: May 20, 2014

(54) SYSTEMS AND METHODS FOR MONITORING RADIATION TREATMENT

(75) Inventors: Ross B. Hannibal, Saratoga, CA (US); Julie Clift, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 646 days.

(21) Appl. No.: 12/868,357

(22) Filed: Aug. 25, 2010

(65) Prior Publication Data

US 2011/0249088 A1    Oct. 13, 2011

Related U.S. Application Data

(60) Provisional application No. 61/323,772, filed on Apr. 13, 2010.

(51) Int. Cl.
| A61B 6/02 | (2006.01) |
| A61B 6/04 | (2006.01) |
| A61B 6/10 | (2006.01) |
| A61B 5/06 | (2006.01) |

(52) U.S. Cl.
CPC . *A61B 5/066* (2013.01); *A61B 6/04* (2013.01); *A61B 6/0457* (2013.01)
USPC .......................................................... 348/77

(58) Field of Classification Search
CPC ......... A61B 5/066; A61B 6/04; A61B 6/0457
See application file for complete search history.

(56) References Cited

U.S. PATENT DOCUMENTS

| 3,720,817 | A | * | 3/1973 | Dinwiddie ........................ 600/1 |
| 4,262,306 | A | * | 4/1981 | Renner ............................ 348/77 |
| 5,446,548 | A | * | 8/1995 | Gerig et al. .................... 356/620 |
| 5,485,502 | A | * | 1/1996 | Hinton et al. .................. 378/117 |
| 5,724,400 | A | * | 3/1998 | Swerdloff et al. ............... 378/65 |
| 5,727,554 | A | * | 3/1998 | Kalend et al. ................. 600/587 |
| 5,818,902 | A | * | 10/1998 | Yu .................................... 378/65 |
| 6,222,544 | B1 | * | 4/2001 | Tarr et al. ....................... 715/839 |
| 6,470,207 | B1 | * | 10/2002 | Simon et al. ................... 600/426 |
| 6,590,477 | B1 | * | 7/2003 | Elco ............................... 333/239 |
| 6,662,036 | B2 | * | 12/2003 | Cosman ......................... 600/411 |
| 6,714,841 | B1 | * | 3/2004 | Wright et al. ................. 700/259 |
| 7,046,765 | B2 | * | 5/2006 | Wong et al. .................... 378/117 |
| 7,103,145 | B2 | * | 9/2006 | Wong et al. .................... 378/117 |
| 7,116,813 | B2 | * | 10/2006 | Funahashi ..................... 382/132 |
| 7,199,382 | B2 | * | 4/2007 | Rigney et al. ............. 250/492.1 |

(Continued)

OTHER PUBLICATIONS

Bejczy et al. "The Phantom Robot: Predictive Displays for Teleoperation with Time Delay" (1990) Jet Propulsion Laboratory, California Institute of Technology.*

(Continued)

*Primary Examiner* — Sath V Perungavoor
*Assistant Examiner* — Matthew J Anderson
(74) *Attorney, Agent, or Firm* — Houst Consulting

(57) ABSTRACT

A method of monitoring radiation treatment employs a video camera directed to at least a portion of a patient and/or patient support and at least a portion of a radiation machine. The direction of movement of the radiation machine and/or clearance between at least a portion of the radiation machine and the patient are determined by a control system. Graphics indicating the direction of movement of the machine and/or the clearance between the machine and the patient are overlaid on the video images. The video images overlaid with graphics displayed on a display.

20 Claims, 3 Drawing Sheets

(56) References Cited

U.S. PATENT DOCUMENTS

| | | | |
|---|---|---|---|
| 7,217,276 B2* | 5/2007 | Henderson et al. | 606/130 |
| 7,446,328 B2* | 11/2008 | Rigney et al. | 250/492.3 |
| 7,657,304 B2* | 2/2010 | Mansfield et al. | 600/427 |
| 7,741,802 B2* | 6/2010 | Prisco et al. | 318/568.11 |
| 7,773,788 B2* | 8/2010 | Lu et al. | 382/128 |
| 7,835,011 B2* | 11/2010 | Dunham | 356/500 |
| 7,984,715 B2* | 7/2011 | Moyers | 128/857 |
| 7,996,064 B2* | 8/2011 | Simon et al. | 600/427 |
| 8,002,465 B2* | 8/2011 | Ahn | 378/205 |
| 8,184,773 B2* | 5/2012 | Cheng et al. | 378/117 |
| 8,223,920 B2* | 7/2012 | Amelia et al. | 378/65 |
| 8,269,195 B2* | 9/2012 | Rigney et al. | 250/492.3 |
| 8,611,983 B2* | 12/2013 | Glossop | 600/424 |
| 2002/0051513 A1* | 5/2002 | Pugachev et al. | 378/65 |
| 2004/0081341 A1* | 4/2004 | Cherek et al. | 382/128 |
| 2005/0065653 A1* | 3/2005 | Ban et al. | 700/245 |
| 2007/0182589 A1* | 8/2007 | Tran | 340/961 |
| 2009/0067577 A1* | 3/2009 | Rigney et al. | 378/65 |
| 2009/0070936 A1* | 3/2009 | Henderson et al. | 5/601 |
| 2009/0180589 A1* | 7/2009 | Wang et al. | 378/65 |
| 2010/0091948 A1* | 4/2010 | Balakin | 378/65 |

OTHER PUBLICATIONS

McShan, D. L. et al. "Advanced Interactive Planning Techniques for Conformal Therapy: High Level Beam Descriptions and Volumetric Mapping Techniques." (1995) Int. J. Radiation Oncology Biol. Phys., vol. 33, No. 5, pp. 1061-1072.*

Brahme et al., "4D laser camera for accurate patient positioning, collision avoidance, image fusion and adaptive approaches during diagnostic and therapeutic procedures," Medical Physics, May 2008, vol. 35, No. 5, pp. 1670-1681.

European Patent Office, European Search Report and Written Opinion in European Application No. 11161610.8, Jul. 22, 2011, 3 pages.

European Patent Office, Communication under Rule 71(3) EPC, Jan. 20, 2014, 30 pages.

* cited by examiner

SYSTEMS AND METHODS FOR MONITORING RADIATION TREATMENT

BACKGROUND

This invention relates in general to the field of radiation treatment, and in particular, to improvement of physical safety of patients during treatment delivery.

Radiation therapy has become increasingly complex in recent years, and remote automation is becoming the norm. Preventing collision between the patient and radiation machine is a key safety aspect and becoming increasingly important. For instance, during radiation delivery inside a treatment room a linear accelerator may rotate around a patient at close clearance to the patient, especially if the patient is large. It would be desirable to have a system and method that can provide clearance information to a radiotherapist who remotely controls the operation outside the treatment room. It would be desirable to have a system and method that can provide information on both current clearance at real time and upcoming clearance in a predictive manner to help the therapist monitor the treatment and prevent collision between the patient and radiation machine.

SUMMARY

The present invention provides a live view system that allows a radiotherapist to clearly see clearances between a patient and a radiation machine from outside the treatment room. A video camera may be mounted in the treatment room directed to at least a portion of the patient. The video camera may be coupled to a computer which may be configured to overlay graphics on the video images from the camera and display the images overlaid with graphics on a treatment screen outside the treatment room to help the radiotherapist monitor the clearances.

The overlaid graphics may indicate the movement of the treatment room equipment such as the gantry, imagers, and couch, and their proximity to each other and the patient. Appropriate graphics or notations may be used to show planned movement and/or current movement, or if desired past movement in conjunction with a replay. In some embodiments directional arrows and other means may be used to indicate motion. The directional arrows may be colored to indicate different types of motion. In some embodiments a transparent virtual LINAC showing arrows and components that have tight clearance may be displayed as this may provide a good view of the patient while providing clear indications of potential movement and tight clearance between the patient and equipment. The live view system of the invention allows a radiotherapist to clearly see the machine/patient clearances within the field of view of the therapist. The live view system also allows a therapist to see the direction the equipment will move while maintaining a clear view of the patient and the treatment parameters.

The live view system may have a virtual model of the equipment. The virtual model may include the geometry of the equipment placed on coordinate systems. The system can show tight clearances to the operator by determining the likely clearances based on the outside surfaces of the virtual model. In some embodiments the virtual model can be used in a predictive manner to determine upcoming clearances. In some embodiments the virtual model can be used in a real-time manner to determine current clearances.

In the situation where the system is used to determine real-time clearances, the system may use the position of the actual equipment to high precision using various feedback devices. The system knows the planned motions based on the electronic treatment instructions. The system can overlay directional arrows, which show the direction of the next move, over the correct locations of the actual machine by using the virtual model. If there are no close clearances, the system may show only the virtual arrow layer over the live video. If there are tight clearances then the system can also show elements of the virtual machine over the live video feed.

BRIEF DESCRIPTION OF THE DRAWINGS

These and various other features and advantages will become better understood upon reading of the following detailed description in conjunction with the accompanying drawings and the appended claims provided below, where

DETAIL DESCRIPTION

Various embodiments of radiation systems and methods are described. It is to be understood that the invention is not limited to the particular embodiments described as such may, of course, vary. An aspect described in conjunction with a particular embodiment is not necessarily limited to that embodiment and can be practiced in any other embodiments. For instance, while various embodiments are described in connection with X-ray radiotherapy machines, it will be appreciated that the invention can also be practiced in other electromagnetic apparatuses and modalities. It is also to be understood that the terminology used herein is for the purpose of describing particular embodiments only, and is not intended to be limiting since the scope of the invention will be defined by the appended claims, along with the full scope of equivalents to which such claims are entitled. In addition, various embodiments are described with reference to the figures. It should be noted that the figures are intended to facilitate the description of specific embodiments and they are not intended as an exhaustive description or as a limitation on the scope of the invention.

As used herein the term "graphic" refers to any symbol of any design, pattern, color, or the like that can be overlaid on a video feed, and may include either pictorial and/or text images.

As used herein the term "transparent" refers to a property of a graphic overlaid on a video feed that allows light to transmit therethrough so that images beyond or behind the graphic can be distinctly seen.

Figure 1:
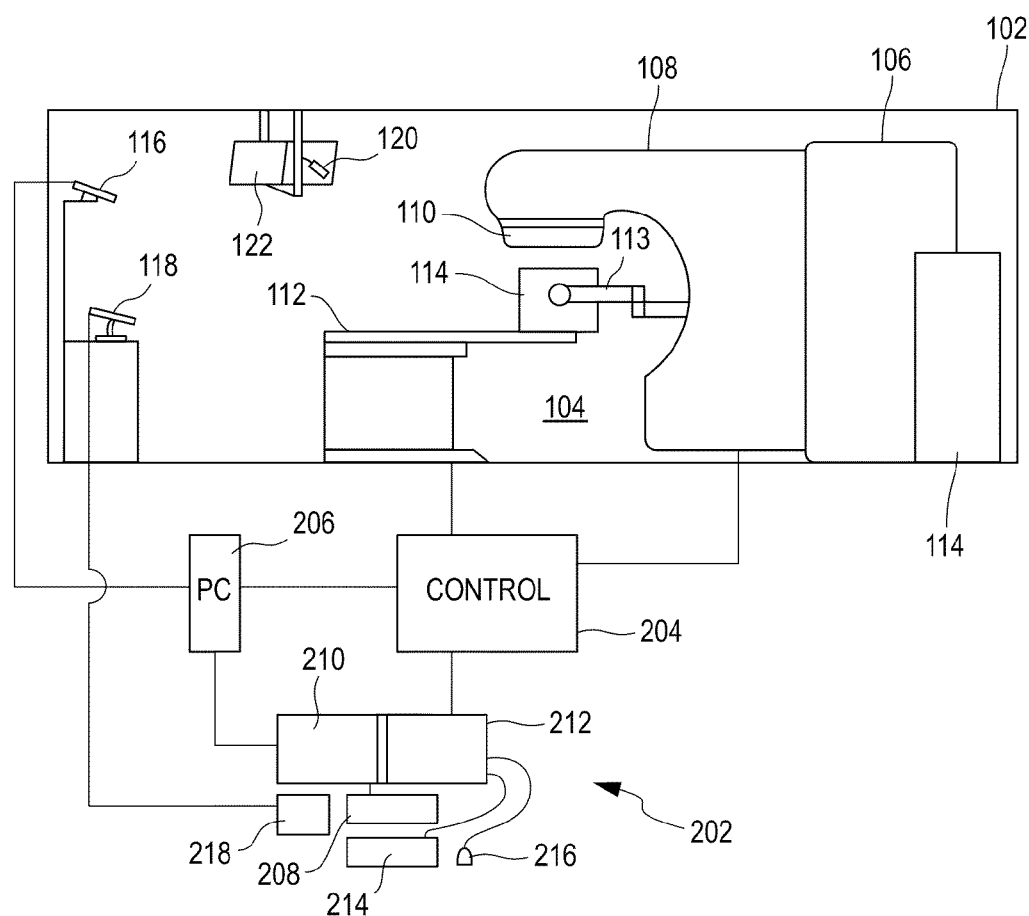
FIG. 1 is a schematic diagram illustrating a radiation system in accordance with some embodiments of the invention.

FIG. 1 illustrates a treatment room 102 and a console area 202 outside the treatment room. The treatment room 102 contains a radiation machine 104 which may include a stand 106, a gantry 108, a collimation assembly 110, a couch 112, and optionally one or more imaging systems 114. The stand 106 may contain components that produce high levels of radio-frequency energy for generating beams. It may also house a water distribution system, a gas pressurizing system, and additional power supplies. The gantry 108 may contain a radiotherapy beam delivery system, which may include a linear accelerator, a bend magnet, an ion chamber, and other beam generation, monitoring, and adjustment devices. The gantry 108 may also support one or more imager arms 113 supporting one or more imaging systems 114. The collimation assembly 110 at the end of the gantry 108 may include a built-in collimator that controls the overall size of the radiation beam, and a multileaf collimator (MLC) that provides fine adjustments to the size and shape of the beam. Collimator accessories may be attached to the collimation assembly 110 to help shape the beam based on a treatment plan. The imaging systems 114 when included allow verification of patient positioning and patient treatment delivery. The imaging systems 114 may include an MV imaging system and a kV imaging system. The MV imaging system may include an MV image detector that can be extended from the base of the gantry 108. The MV image detector may acquire data from beams generated through the accelerator. The kV imaging system may include a kV source and a kV image detector mounted on the sides of the gantry 108. The images acquired by the imaging systems 114 may be displayed on a display 212 in the console area 202 and compared with reference images created during simulation and treatment planning sessions. The patient's position may be adjusted based on the acquired images before delivering the treatment. The patient couch 112 may be equipped with various mechanisms that allow precise positioning of the patient for imaging and treatment. The couch 112 may translate and rotate in three dimensions. A modulator cabinet 114, which may be located in the treatment room 102 or in a separate room, may contain components that transform hospital power into the high-voltage electricity the radiation system 104 may require. While not shown in FIG. 1, a plurality of feedback devices may be mounted on the machine components to provide information of positions of various machine components or motion axes.

The treatment room 102 may contain one or more cameras to perform various monitoring functions. For example, a camera 116 may be mounted in the treatment room 102 to aim at the patient or at least a portion of the patient. The camera 116 may provide video images of at least a portion of the patient and/or the couch, and at least a portion of the radiation machine. The camera 116 may be coupled to a computer 206, which may overlay graphics on the images from the camera 116 to provide additional information such as the direction or speed of movement of the machine or collision alert etc. The images overlaid with graphics may appear on a display 210 in the console area 202 to allow a radiotherapist to watch the patient closely at all times during the treatment. Hereafter the camera 116 may be referred to as the live view camera.

One or more additional cameras 118 may be mounted in the treatment room 102 to provide view of clearance along both sides of the couch 112. The one or more additional cameras 118 may be placed in a way that both the patient and the clearance between the machine and the patient can be monitored easily. The images from the cameras 118 may appear on one or more closed-circuit TV monitors 218. The monitors 218 may be placed in the console area 202 in a way to be effective in monitoring clearances between the machine and the patient. A radiotherapist may use the video images from the cameras 118 to check clearances to avoid possible collisions. Hereafter the cameras 118 may be referred to as motion view cameras.

The treatment room 102 may also contain a respiratory gating camera 120 for monitoring the motion of a set of reflective markers placed on the patient. One or more in-room monitors 122 may be provided to display information such as the machine parameter information including planned and actual axis positions that a radiotherapist may need while inside the treatment room. The monitors 122 may be mounted e.g. side by side so that the radiotherapist can easily observe the data while still watching the patient.

A control system 204 for controlling the operation of the radiation machine 104 may be placed outside the treatment room 102. The control system 204 may include a computer comprising a memory and a processor such as a digital signal processor (DSP), a central processing unit (CPU), or a microprocessor (μP), and may be operated by a computer software interface such as a graphical user interface (GUI). The memory may store treatment plan information and programs for operating the radiation machine 104 or various elements of the machine. The treatment plan may be created in a treatment planning session and may include information such as the nature of a tumor including the size, shape, and location of the tumor in the patient, the treatment dose to be delivered, and the position, angle, and/or movement of the treatment machine 104 with respect to the patient etc. The treatment plan information may be used by the computer 206 to overlay graphics on the video feed from the live view camera 116 to indicate additional information such as the direction of movement of the machine as will be described in greater detail below.

The control system 204 may be provided with a proximity detection or collision protection program for collision detection, distance computation, and/or contact determination of the machine elements undergoing movement such as the rotating gantry and moving couch etc. Various proximity detection programs known in the art may be used. The control system 204 may use the proximity detection program to compute collision alert information and provide it to the computer 206, which in turn may overlay the collision alert information on the video feed from the live view camera 116, as will be described in greater detail below.

The computer 206 may be coupled to the live view camera 116 and configured to receive video feed from the live view camera 116. The computer 206 may be provided with a treatment application program configured to display the video feed on a display 210, overlay graphics on the video feed, or perform other graphical enhancement of the video images including adding graphics, deleting or modifying video images etc. The techniques for graphical enhancement of video images are known in the art and their detail description is omitted in order to focus on the description of the invention.

The computer 206 may be provided with a 3-D model of the radiation machine 104. The 3-D model of the machine 104 may be created using various computer programs known in the art. In creating the 3-D model, the dimensions of the machine 104 may be measured and the positions of the machine components determined in a coordinate system. For example, a coordinate system may be first established using the isocenter as the origin and the beam direction as the z-axis. The machine 104 or machine elements such as the patient couch 112, rotating gantry 108, and imagers 114 etc. may be measured in the coordinate system, providing the x, y, and z values for numerous data points of the machine or machine elements. The dimension and position data of the machine 104 in the coordinate system may then be provided to a computer program to create a 3-D model of the machine. The elements of the 3-D model may be preconfigured in configuration files and the geometry of each machine element may be defined e.g. using virtual reality modeling language (VRML) or other suitable program languages. These files may be loaded to the computer 206, which may create a 3-D view of the radiation machine 104.

Prior to graphical enhancement the computer control 206 may be calibrated to identify the position and orientation of the live view camera 116 with respect to the radiation machine 104. The calibration determines how the 3-D model of the radiation machine 104 may be displayed over the images from the live view camera 116 so that the two images can match up. To perform the live view calibration, a calibration target such as a positioning marker may be placed on the machine 104 such as on the patient couch 112 at the isocenter position. The couch 112 may then be moved to a number of known calibration positions. The position of the calibration target in the video image may be identified at each of the calibration positions and this information can be used to calculate the position of the live view camera 116 relative to the radiation machine 104. The calibration results may be saved and the treatment application may use the results to determine the location and size of the 3-D model of the machine loaded in the computer 206. Live view calibration may be performed initially when the system is setup and thereafter whenever the camera 116 is moved. The calibration results may be tightly bound to the camera angle and position, therefore a calibration procedure should be performed whenever the camera 116 is moved. A calibration wizard control may include a pop-up window that implements the calibration workflow. It may follow a wizard paradigm with individual screens that guide a user through each step of the calibration process. On successful calibration, the live view calibration files may be updated.

In some embodiments, the computer control 206 may overlay graphics on the video feed from the live view camera 116 to indicate the direction of movement of the machine 104 including the movement of the gantry 108, the couch 112, and the imaging systems 114 etc. The graphics overlaid may indicate the direction of current movement of the machine 104, or the direction of planned or upcoming movement of the machine 104. If desired, the graphics may also indicate the past movement of the machine 104 in conjunction with a replay. The machine's current position may be determined using various feedback devices mounted on the machine 104. The control system 204 may receive signals from the feedback devices, determine the current position of the machine, and provide the information to the computer 206, which may in turn overlay graphics on top of the video images. The machine's upcoming movement direction may be calculated by the control system 204 using information of the machine's current position and planned position. The machine's planned position may be provided by the treatment plan which may be determined in a treatment planning session. The control system 204 may feed the calculated information to the computer 206, which may then overlay graphics indicating the direction of the machine's upcoming movement on the video feed. The graphics indicating the direction of movement of the machine, either at real time or in a predicative manner, may allow a radiotherapist to quickly determine the correct area that it may need to watch, and thus help the radiotherapist monitor the clearance between the patient and the machine more easily.

The graphic indicating the direction of machine movement may be in form of arrows or in any other appropriate shapes and forms, or in text. The directional arrows or other appropriate shapes, forms or text may be colored to indicate different types of machine motion. By way of example, orange color may be used to show equipment before motion, and as it moves to target positions. Blue color may be used to show dynamic motion when an automated gantry move is performed such as for cone-beam computed tomography imaging or arc and automated treatments. Yellow color may be used to indicate that the moving equipment is approaching a possible collision with other equipment or the patient. Pink color may be used to indicate that the equipment is too close to other equipment or the patient, or collision is imminent, in which case motion stops. Instead of color, other means such as size, shape or other characteristic of graphical means can be used to indicate differing types of motion.

In some embodiments the graphics overlaid on the video feed may be substantially transparent so that the video images behind or beyond the graphics can be distinctly seen. Transparent graphics may be advantageous in that they can provide a clear view of current positions of the patient and the machine while providing indications of potential movement of the machine or tight clearance between the patient and the machine.

In some embodiments, the computer control 206 may overlay graphics on the video images to indicate collision alert or collision detected information. Using a proximity detection program and a 3-D model of the machine, the control system 204 may compute distances between the machine and the patient or between machine elements using information of actual positions of the machine detected through various feedback devices at real time. By way of example, if the computed distance is within a predetermined range the control system 204 may generate a collision alert. If the computed distance is equal to or less than a predetermined value the control system 204 may generate a collision detected. The collision alert or collision detected information may be provided to the computer 206, which may then overlay a graphic on the video feed and display it on a display 210.

The graphic indicating the collision alert or collision detected may be in any suitable shapes, forms, text, and colors, with or without sounds. For example, yellow color may be used to indicate collision alert, and pink color may be used to indicate collision detected, in which case the machine motion may stop. The graphic may blink on a display 210 or may be accompanied with an emergency alarm to alert the radiotherapist. In some embodiments, a transparent virtual 3-D model of the machine or a portion of the machine may be overlaid on the video feed to show the tight clearance between the patient and machine.

Other different graphical schemes showing any other parameters of the machine or patient of interest may be overlaid on the video image. For example, graphical means indicating the velocity of the machine can be added. As another example, graphical means may be added to indicate timing or order of various motions, including by adding notations, such as numerals indicating order, or timers providing total time of motion, countdown until beginning of motion, or time remaining for a particular movement. In general, any of the foregoing means and the means described above for indicating different types of motion may be used for any of the parameters of interest.

Figure 2:
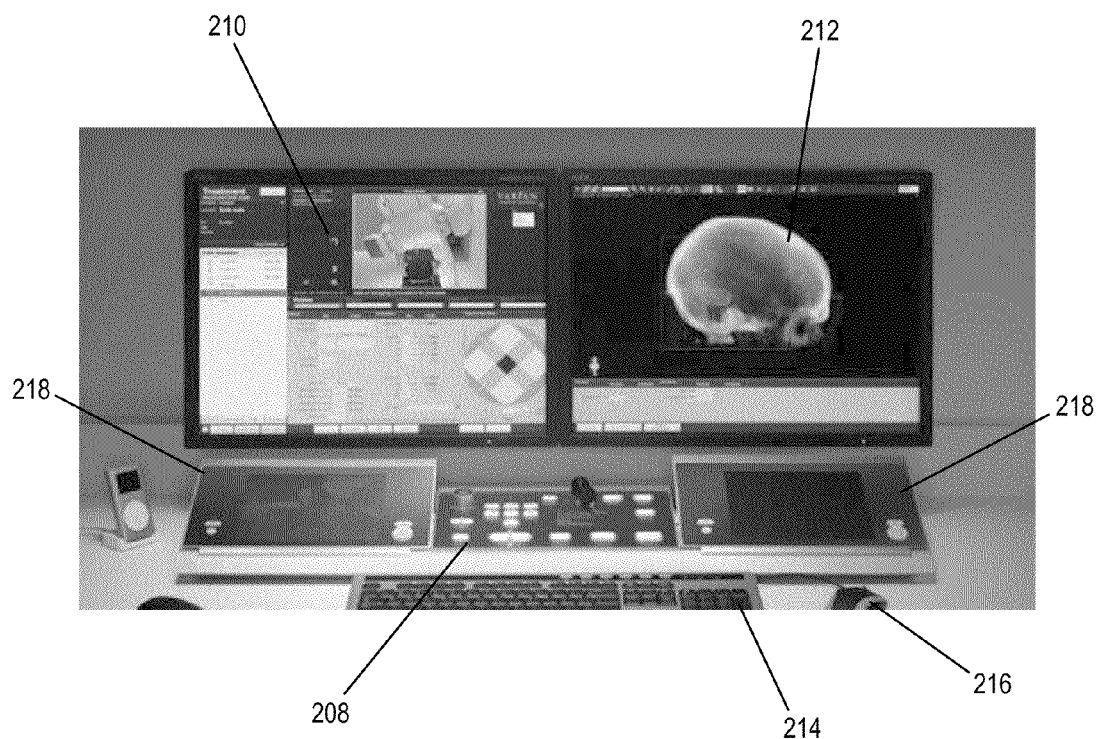
FIG. 2 is an illustration of an exemplary console area in accordance with some embodiments of the invention.

The console area 202 may include a control console 208, a first display 210 for displaying treatment information (hereafter "treatment screen"), a second display 212 for displaying imaging information (hereafter "imaging screen"), and a keyboard 214 and a mouse 216 for input of commands and/or text by a user. One or more closed-circuit TV monitors 218 may be placed in a close proximity to the control console 208. An exemplary overall layout of the console area is illustrated in FIG. 2.

The control console 208 contains buttons and keys that provide controls for the motion of the machine 104, intercom, image acquisition, and treatment delivery. The control console 208 allows a radiotherapist to remotely move the radiation machine 104 including the gantry 108, patient couch 112 and other equipment in the treatment room 102. The control console 208 may include an emergency stop which when pressed may turn off the system in case of emergency. In case that the machine 104 is equipped with imaging systems 114, the control console 208 may include buttons for selection between MV and kV imagers.

Figure 3:
FIGS. 3-4 are exemplary screenshots of video images overlaid with graphics indicating directions of movement of a radiation machine in accordance with some embodiments of the invention.
Figure 4:
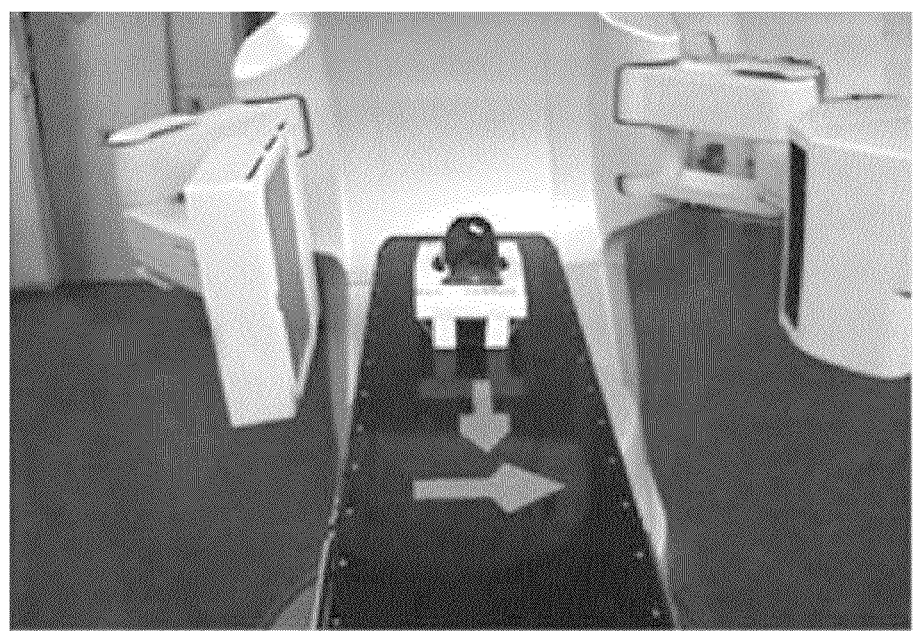

The treatment screen 210 may display patient data, treatment plan, beam parameters and eye view, and collimator settings etc. The video images from the live view camera 116 on which graphics of information may be overlaid according to the invention, may be displayed on the treatment screen 210 so that the video feed of the patient and the machine may be readily viewed along with treatment information in the console area 202. FIGS. 3-4 are partial enlarged screenshots of video images displayed on the treatment screen 210. In this example, directional arrows are overlaid on the video images to show direction of movement of the patient table.

The imaging screen 212, which may be placed on a side of the treatment screen 210, displays imaging parameters and patient images including reference images and acquired images. A radiotherapist may use the imaging screen to determine if the patient needs to be repositioned. The closed-circuit TV monitors 218 may be located in a close proximity to the treatment screen 210 so that a radiotherapist may readily view the images from the motion view cameras 118 in monitoring the clearance between the patient and the machine.

The system and method of the invention described above facilitates monitoring and thus helps prevent collision between the machine and the patient during radiation treatment. A radiation treatment may involve complex motion of a couch that the patient is on and complex motion of a linear accelerator including a gantry and imaging arms etc. Prior to treatment a therapist may move the couch, gantry, and imaging arms from inside the treatment room. During this time the therapist may have a good view of the clearances and collisions are unlikely. Just prior to the treatment the therapist may leave the treatment room and view the clearance from closed-circuit TV cameras. During the beam-on the gantry, imagers, and couch may move. After the first beam-on the therapist may move the equipment to a second treatment position and again the gantry, imagers, and couch may move. In both cases it would be desirable if the therapist knows the direction of motion of the gantry, imagers, or couch so that it can look at the correct area to monitor the clearance between the equipment and the patient. The live view system of the invention can be advantageously used for this purpose and other applications. A live view camera may be placed in the treatment room to provide a general view of the equipment and the patient. The video feed from the live view camera may be overlaid with graphics indicating the direction of current or upcoming movement of the machine. The video feed overlaid with graphics may be displayed on the treatment screen in the console area so that a therapist may monitor easily.

Transparent virtual graphics such as directional arrows overlaid on the live video images provide a clear indication of motion without significantly covering up the video images of the patient. For a therapist, a clear view of the video images is important so it can keep an eye on the patient. The therapist needs to see the actual equipment in relation to the patient to check clearance. The minimal obstruction of the virtual arrows or other graphics assures a clear view of the patient. In the case where the clearance is tight the machine speed may be automatically reduced and a live view screen region may show a virtual model layer of the elements(s) of the machine where the clearance is tighter than a pre-defined tolerance. These virtual elements can provide a clear indication for the therapist to where they need to look to closely watch clearance. If the clearance is too tight, the machine may prevent remote motion, i.e., motion outside the treatment room. In this situation, the therapist may enter the treatment room to complete the motion.

Those skilled in the art will appreciate that various other modifications may be made within the spirit and scope of the invention. All these or other variations and modifications are contemplated by the inventors and within the scope of the invention.

What is claimed is:

1. A method of monitoring radiation treatment, comprising:
   providing video images of at least a portion of a patient and/or patient support and at least a portion of a radiation machine;
   determining a direction of a current movement of the radiation machine relative to the patient in a radiation treatment at least based on a treatment plan;
   overlaying a graphic on the video images to indicate the direction; and
   displaying the video images overlaid with the graphic on a display.

2. The method of claim 1 further comprising the steps of determining a direction of upcoming movement of the radiation machine relative to the patient, and overlaying a graphic indicating the direction of upcoming movement of the radiation machine determined.

3. The method of claim 1 wherein the overlaying step comprises overlaying a directional arrow indicating the direction of movement of the radiation machine determined.

4. The method of claim 1 wherein the overlaying step comprises overlaying a colored graphic.

5. The method of claim 1 wherein the overlaying step comprises overlaying a transparent graphic.

6. The method of claim 1 wherein said radiation machine includes a rotatable gantry, an imager, and a couch, the determining step comprises determining a direction or directions of movement of the gantry, imager, and/or couch, and the overlaying step comprising overlaying a transparent directional arrow or arrows indicating the direction or directions of movement of the gantry, imager, and/or couch.

7. The method of claim 1 wherein the displaying step comprises displaying treatment information on the display which displays the video images overlaid with the graphic, the treatment information including information about the patient, treatment plan for the patient, and parameters of the radiation machine.

8. A radiation system, comprising:
   a radiation machine;
   a control system operable to control the radiation machine;
   a video camera directed to at least a portion of the radiation machine and a subject to be treated by the radiation machine;
   a computer coupled to the video camera adapted to overlay a graphic representing a direction of movement of the radiation machine and clearance between at least a portion of the radiation machine and the subject on video images from the video camera; and
   a display for displaying the video images overlaid with the graphic.

9. The radiation system of claim 8 wherein said display is further adapted to display treatment information including information about a patient, a treatment plan for the patient, and parameters of the radiation machine.

10. The radiation system of claim 8 wherein said radiation machine and video camera are placed in a treatment room, and said display is placed outside of the treatment room.

11. The radiation system of claim 10 further comprising one or more additional video cameras in the treatment room directed to at least a portion of the machine and the patient, and one or more additional closed-circuit TV monitors outside of the treatment room for displaying video images from the one or more additional video cameras.

12. The radiation system of claim 11 wherein said one or more additional close-circuit TV monitors are placed in a close proximity to the display which displays the video images overlaid with the graphic.

13. The radiation system of claim 8 wherein said radiation machine comprises a couch and a gantry containing a radiation source, said couch and gantry being movable relative to each other.

14. The radiation system of claim 13 wherein the radiation machine further comprises an imaging system, and the radiation system further comprises an additional display for displaying images acquired by the imaging system, said additional display being placed in a close proximity to the display which displays the video images overlaid with the graphics.

15. A method of monitoring radiation treatment, comprising:
providing video images of at least a portion of a patient and/or patient support and at least a portion of a radiation machine;
determining a direction of movement of the radiation machine in a radiation treatment at least based on a treatment plan;
overlaying a graphic on the video images to indicate the direction; and
displaying the video images overlaid with the graphic on a display; the method further comprising:
determining a clearance between at least a portion of the radiation machine and the patient in a radiation treatment;
overlaying a graphic on the video images to indicate the clearance; and
displaying the video images overlaid with the graphic indicating the clearance on the display.

16. The method of claim 15 wherein the overlaying step comprises overlaying a graphic of collision alert if the clearance determined is within a predetermined range.

17. The method of claim 16 wherein the overlaying step further comprises overlaying a transparent graphic of at least a portion of a 3-D representation of the radiation machine on the video images.

18. The method of claim 15 wherein the overlaying step comprises overlaying a graphic of collision detected if the clearance determined is equal to or less than a predetermined value.

19. The method of claim 18 wherein the overlaying step further comprises overlaying a transparent graphic of at least a portion of a 3-D representation of the radiation machine on the video images.

20. The method of claim 19 further comprising the step of suspending movement of the radiation machine.

* * * * *